United States Patent
Konishi et al.

(10) Patent No.: US 10,588,849 B2
(45) Date of Patent: Mar. 17, 2020

(54) COSMETIC COMPOSITION

(71) Applicant: SHIN-ETSU CHEMICAL CO., LTD., Tokyo (JP)

(72) Inventors: Masayuki Konishi, Tokyo (JP); Chihiro Hayakawa, Tokyo (JP); Akiko Mizuno, Tokyo (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 75 days.

(21) Appl. No.: 15/571,995

(22) PCT Filed: Apr. 25, 2016

(86) PCT No.: PCT/JP2016/062887
§ 371 (c)(1),
(2) Date: Nov. 6, 2017

(87) PCT Pub. No.: WO2016/178380
PCT Pub. Date: Nov. 10, 2016

(65) Prior Publication Data
US 2018/0133141 A1    May 17, 2018

(30) Foreign Application Priority Data

May 7, 2015 (JP) ................................. 2015-094916

(51) Int. Cl.
| | | |
|---|---|---|
| A61K 8/00 | (2006.01) | |
| A61K 8/891 | (2006.01) | |
| A61Q 17/04 | (2006.01) | |
| A61Q 19/00 | (2006.01) | |
| A61Q 1/06 | (2006.01) | |
| A61Q 1/02 | (2006.01) | |
| A61K 8/892 | (2006.01) | |
| A61K 8/02 | (2006.01) | |
| A61K 8/06 | (2006.01) | |
| A61K 8/19 | (2006.01) | |

(52) U.S. Cl.
CPC .............. *A61K 8/891* (2013.01); *A61K 8/022* (2013.01); *A61K 8/064* (2013.01); *A61K 8/19* (2013.01); *A61K 8/892* (2013.01); *A61Q 1/02* (2013.01); *A61Q 1/06* (2013.01); *A61Q 17/04* (2013.01); *A61Q 19/00* (2013.01); *A61K 2800/413* (2013.01)

(58) Field of Classification Search
None
See application file for complete search history.

(56) References Cited

U.S. PATENT DOCUMENTS

| | | | |
|---|---|---|---|
| 2007/0128137 A1 | 6/2007 | Yoshimi et al. | |
| 2009/0238781 A1* | 9/2009 | Sakuta | A61K 8/066 424/59 |
| 2010/0172850 A1 | 7/2010 | Mitsui | |
| 2011/0104222 A1* | 5/2011 | Iida | A61K 8/375 424/401 |
| 2012/0301417 A1 | 11/2012 | Pays et al. | |
| 2014/0004164 A1* | 1/2014 | Mundschau | A61K 8/06 424/401 |

FOREIGN PATENT DOCUMENTS

| | | |
|---|---|---|
| JP | 2002-003334 A | 1/2002 |
| JP | 2007-182402 A | 7/2007 |
| JP | 2008-143823 A | 6/2008 |
| JP | 2009-536966 A | 10/2009 |
| JP | 2009-256616 A | 11/2009 |
| JP | 2013-035872 A | 2/2013 |
| JP | 2013-095705 A | 5/2013 |
| JP | 2013-216703 A | 10/2013 |

OTHER PUBLICATIONS

International Search Report (PCT/ISA/210) issued in PCT/JP2016/062887, dated Aug. 2, 2016.
Written Opinion (PCT/ISA/237) issued in PCT/JP2016/062867, dated Aug. 2, 2016.
"Shin Etsu Unique Materials. Silicone Products for Personal Care," Internet Citation (Feb. 1, 2008), 20 pages, XP007906619, retrieved from Internet: URL:http://www.shinetsusilicones.com/SESA%20Personal%20Care%20Unique%20Material.pdf [retrieved on Dec. 12, 2008], pp. 3, 4, 6, 16.
Extended European Search Report dated Nov. 30, 2018, in European Patent Application No. 16789516.8.

* cited by examiner

*Primary Examiner* — Susan T Tran

(74) *Attorney, Agent, or Firm* — Birch, Stewart, Kolasch & Birch, LLP

(57) ABSTRACT

Provided is a cosmetic composition formed from a silicone-branched polyglycerol-modified silicone, of which the weight-average molecular weight, in terms of polystyrene, does not exceed 10,000 according to gel permeation chromatography.

7 Claims, No Drawings

COSMETIC COMPOSITION

TECHNICAL FIELD

The present invention relates to a cosmetic composition. In this invention, compositions for cosmetics (cosmetic compositions) are sometimes referred to simply as "cosmetics."

BACKGROUND ART

In cosmetics, silicone surfactants modified with glycerol or polyglycerol typically have an excellent performance in terms of moisturizing properties, but are known to have a tendency to produce a sticky feel on the skin.

Also, metal oxide powders such as titanium dioxide and zinc oxide improve transparency and increase the ultraviolet-blocking effect, and so finely divided metal oxide powders having an average particle size of 100 nm or less are widely used in sunscreen cosmetics. However, the larger surface area of finely divided metal oxide powders increases bonding forces between particles, as a result of which such powders tend to readily agglomerate. Hence, when these finely divided metal oxide powders are used in sunscreen cosmetics, their ability to be stably included without agglomerating is important. Generally, in cosmetics, art for enhancing the stability of formulations by including glycerol-modified silicone surfactants (Patent Document 2) and art for enhancing the stability of formulations by the combined use of a glycerol-modified silicone surfactant and trimethylsiloxysilicic acid (Patent Document 3) is known. However, the glycerol-modified silicones used here have a large molecular weight, and have been inadequate for enhancing the stability of formulations.

PRIOR ART DOCUMENTS

Patent Documents

Patent Document 1: JP-A 2002-3334
Patent Document 2: JP-A 2013-035872
Patent Document 3: JP-A 2007-182402

SUMMARY OF THE INVENTION

Problems to be Solved by the Invention

It is therefore an object of the present invention to provide cosmetic compositions which contain polyglycerin-modified silicones that feel good on the skin, minimize agglomeration during powder dispersion, and confer excellent formulation stability.

Means for Solving the Problems

The inventors have conducted extensive investigations aimed at achieving the above object. As a result, they have discovered that when a low-molecular-weight silicone-branched polyglycerin-modified silicone is included within a cosmetic composition, the composition feels good on the skin and, particularly in powder-containing cosmetics, the dispersibility improves, thereby giving the composition a low viscosity, holding down stickiness and achieving excellent formulation stability.

Accordingly, the invention provides the following cosmetic compositions.

[1] A cosmetic composition comprising a silicone-branched polyglycerin-modified silicone having a polystyrene-equivalent weight-average molecular weight, as determined by gel permeation chromatography, which is not more than 10,000.
[2] The cosmetic composition of [1], wherein the silicone-branched polyglycerin-modified silicone is polyglyceryl-3 polydimethylsiloxyethyl dimethicone.
[3] The cosmetic composition of [1] or [2], wherein the polystyrene-equivalent weight-average molecular weight is measured by gel permeation chromatographic analysis under the following conditions: Tosoh Corporation columns, TSKgel Super H2500 and TSKgel Super HM-N; solvent, tetrahydrofuran; flow rate, 0.6 mL/min; detector, RI (40° C.); column temperature, 40° C.; injected amount, 50 µL; sample concentration, 0.3 wt %.
[4] The cosmetic composition of any of [1] to [3] which contains from 0.1 to 20 wt % of silicone-branched polyglycerin-modified silicone, based on the overall cosmetic composition.
[5] The cosmetic composition of any of [1] to 141, further comprising one, two or more types of powder.
[6] The cosmetic composition of [5], wherein the powder is a finely divided metal oxide having an average primary particle size of 200 nm or less.
[7] The cosmetic composition of any of [1] to [6] which is an emulsified composition.
[8] The cosmetic composition of any of [1] to [6] which is a nonaqueous composition.

Advantageous Effects of the Invention

According to this invention, by formulating a cosmetic composition with a silicone-branched polyglycerin-modified silicone having a polystyrene-equivalent weight-average molecular weight, as determined by gel permeation chromatography (GPC), of not more than 10,000, the sticky feel distinctive to surfactants is reduced and, in cosmetic formulations containing a powder, especially a finely divided metal oxide, the powder can be stably dispersed even at a lower viscosity, enabling the stability and usability of cosmetics to be improved.

EMBODIMENT FOR CARRYING OUT THE INVENTION

Embodiments of the invention are described in detail below, although the invention is not in any way limited thereby.

In this invention, the term "cosmetics" is not particularly limited, provided that it denotes cosmetics which include as an essential ingredient the foregoing silicone-branched polyglycerin-modified silicone having a weight-average molecular weight of not more than 10,000. It may be applied to diverse products, including, for example, beauty essences, milky lotions, creams, foundations, makeup bases, concealers, cheek color, lipstick, eye shadow, eyeliner, body makeup and deodorants. The physical form of the inventive cosmetic may be selected from among various forms, such as liquid, cream, solid, paste, gel, mousse, spray and powder forms.

<Silicone-Branched Polyglycerin-Modified Silicone>

The silicone-branched polyglycerin-modified silicone compound used in the invention has general formula (1) below.

$$R^1_a R^2_b R^3_c SiO_{(4-a-b-c)/2} \quad (1)$$

In formula (1). $R^1$ is a substituted or unsubstituted monovalent hydrocarbon group of 1 to 30 carbon atoms, and preferably 1 to 15 carbon atoms, such as an alkyl, aryl, aralkyl, fluorine-substituted alkyl, amino-substituted alkyl or carboxy-substituted alkyl group, or a like or unlike organic group selected from organic groups of general formula (2) below. Of the $R^1$ groups, specific examples of substituted or unsubstituted monovalent hydrocarbon groups include alkyl groups such as methyl, ethyl, propyl, butyl, pentyl, hexyl, heptyl, octyl, nonyl and decyl groups: cycloalkyl groups such as cyclopentyl and cyclohexyl groups; aryl groups such as phenyl and tolyl groups; aralkyl groups such as benzyl and phenethyl groups; and fluorine-substituted alkyl groups such as trifluoropropyl and heptadecafluorodecyl groups. Additional examples include amino-substituted alkyl groups such as 3-aminopropyl and 3-[(2-aminoethyl)amino]propyl groups, and carboxy-substituted alkyl groups such as the 3-carboxypropyl group. Some portion of the $R^1$ groups may be organic groups of general formula (2) below.

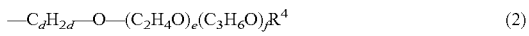
$$-C_dH_{2d}-O-(C_2H_4O)_e(C_3H_6O)_fR^4 \quad (2)$$

Here, $R^4$ is a hydrogen atom, a monovalent hydrocarbon group of 1 to 30 carbon atoms, especially an alkyl group of 1 to 4 carbon atoms such as a methyl group, or $R^5-(CO)-$ (wherein $R^5$ is a monovalent hydrocarbon group of 1 to 30 carbon atoms, especially an alkyl group of 1 to 4 carbon atoms such as methyl). In particular, it is preferable for at least 50 mol % of all $R^1$ groups to be methyl groups, more preferable for at least 70 mol % to be methyl groups, and most preferable for 100 mol % to be methyl groups.

Also, the subscripts d, e and f are respectively integers which satisfy the conditions $0 \le d \le 15$, $0 \le e \le 50$ and $0 \le f \le 50$, the organic group of formula (2) being exemplified by alcohol residues and alkenyl ether adduct residues. For example, when d=0, formula (2) becomes $-O-(C_2H_4O)_e(C_3H_6O)_fR^4$. When e=0 and f=0, the organic group of formula (2) is exemplified by alkoxy groups of 1 to 30 carbon atoms, examples of which range from lower alkoxy groups such as methoxy and butoxy groups to higher alkoxy groups such as the cetyloxy, oleyloxy and stearyloxy groups of cetyl alcohol, oleyl alcohol and stearyl alcohol; and by the fatty acid residues of, for example, acetic acid, lactic acid, butyric acid, oleic acid, stearic acid and behenic acid. When e and f are larger than 1 (e, f>1), the organic group of formula (2) is the alcohol residue of a (hydroxy-terminated) alkylene oxide adduct of a higher alcohol. When d is 1 or more, e=0 and f=0, it is especially preferable for d to be 3, 5 or 11, examples of such organic groups being propyl ether, pentenyl ether and undecenyl ether residues. Depending on the $R^4$ substituent, illustrative examples include the allyl stearyl ether residue, the pentenyl behenyl ether residue and the undecenyl oleyl ether residue. When e or f is not 0, there exists an alkoxy group or ester group bonded through polyoxyalkylene. Here, regardless of what e and f represent, when d is 0, the hydrolysis resistance may be poor, and when d is 15 or more, the oil odor is strong. Hence, d is preferably from 3 to 5.

$R^2$ is a polyglycerol derivative of general formula (3) and/or (4) below.

[Chemical Formula 1]

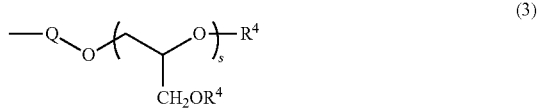

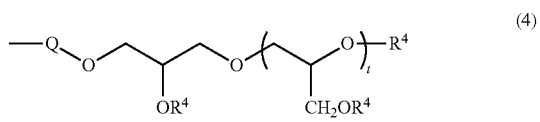

In these formulas, $R^4$ is as defined in formula (2) above, and Q is a divalent hydrocarbon group of 2 to 20 carbon atoms which may include an ether bond and an ester bond, examples of which include $-(CH_2)_2-$, $-(CH_2)_3-$, $-CH_2CH(CH_3)CH_2-$, $-(CH_2)_4-$, $-(CH_2)_5-$, $-(CH_2)_1-$, $-(CH_2)_7-$, $-(CH_2)_8-$, $-(CH_2)_2-CH(CH_2CH_2CH_3)-$, $-CH_2-CH(CH_2CH_3)-$, $-(CH_2)_3-O-(CH_2)_2-$, $-(CH_2)_3-O-(CH_2)_2-O-(CH_2)_2-$, $-(CH_2)_3-O-CH_2CH(CH_3)-$, $-CH_2-CH(CH_3)-COO(CH_2)_2-$. Also, s is an integer from 2 to 10, especially from 2 to 4; and t is an integer from 1 to 10, especially from 1 to 4.

$R^3$ is a silicone-containing group of general formula (5) below.

[Chemical Formula 2]

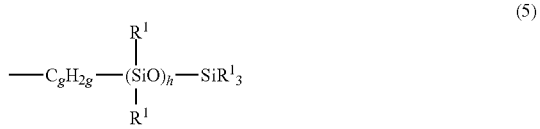

In this formula, $R^1$ is as defined in formula (1) above, and g is an integer from 1 to 5. Particularly in synthesis from a reaction between a vinylsiloxy group and a SiH group, g is 2. The subscript h is from 0 to 500, and preferably from 1 to 50. When h is larger than 500, problems sometimes arise, such as worsening of the reactivity with the main chain.

The subscript "a" is from 1.0 to 2.5, and preferably from 1.2 to 2.3. When "a" is smaller than 1.0, compatibility with oils is poor and water resistance is difficult to achieve; on the other hand, when "a" is larger than 2.5, the hydrophilicity decreases, as a result of which the reactivity with powder is poor, making a stable dispersion difficult to obtain. The subscript "b" is from 0.001 to 1.5, and preferably from 0.05 to 1.0. When "b" is smaller than 0.001, the hydrophilicity decreases, as a result of which reactivity with powder is poor, making stable dispersibility difficult to obtain; on the other hand, when "b" is larger than 1.5, the hydrophilicity becomes too large, making stable dispersibility difficult to obtain. The subscript "c" is from 0.001 to 1.5, and preferably from 0.05 to 1.0. When "c" is smaller than 0.001, the compatibility with silicone oil diminishes, making stable dispersibility difficult to obtain; on the other hand, when "c" is larger than 1.5, the hydrophilicity decreases, as a result of which the reactivity with powder is poor, making stable dispersibility difficult to obtain.

The weight-average molecular weight of the silicone compound of formula (1) is not limited, provided it is not more than 10,000, although a weight-average molecular weight of from 5,000 to 10,000 is preferred. At more than 10,000, the usability worsens. On the other hand, at less than 5,000, there is a possibility that, owing to, for example, an increase in the hydrophilic-lipophilic balance (HLB), a good powder dispersing effect may not be obtained. In the invention, the weight-average molecular weight refers to the polystyrene-equivalent weight-average molecular weight in gel permeation chromatography (GPC), and is preferably measured under the following conditions in GPC analysis: Tosoh Corporation columns, TSKgel Super H2500 (1 column) and TSKgel Super HM-N (1 column); solvent, tetrahydrofuran; flow rate, 0.6 mL/min; detector, RI (40° C.); column temperature, 40° C.; injected amount, 50 µL; sample concentration, 0.3 w %.

The silicone-branched polyglycerin-modified silicone used in this invention is exemplified by polyglyceryl-3 polydimethylsiloxyethyl dimethicone, as defined in the Cosmetic-Info.jp (https://www.cosmetic-info.jp) database, which is not particularly limited provided it has a weight-average molecular weight (Mw) as measured by GPC of not more than 10.000. Commercial products are exemplified by KF-6106 (Mw=8,500) from Shin-Etsu Chemical Co., Ltd.

The amount of silicon-branched polyglycerin-modified silicone, such as polyglyceryl-3 polydimethylsiloxyethyl dimethicone, included in the cosmetic composition of the invention is preferably from 0.1 to 20 wt %, and more preferably from 0.5 to 9 wt %, of the overall weight of the composition.

<Powder>

The powder used in this invention is not particularly limited, provided that it is a powder which can typically be included in cosmetics, such as a pigment. The pigment is not particularly limited, provided it is one that is generally used in makeup cosmetics. Illustrative examples include nonorganic pigments such as talc, mica, kaolin, silica, calcium carbonate, zinc white, titanium dioxide, red iron oxide, yellow iron oxide, black iron oxide, ultramarine, Prussian blue, carbon black, titanium suboxide, cobalt violet, chromium oxide, chromium hydroxide, cobalt titanate, bismuth oxychloride and titanium-mica pearlescent pigments; organic pigments, including zirconium, barium or aluminum lakes such as Red No. 201, Red No. 202, Red No. 204, Red No. 205, Red No. 220, Red No. 226, Red No. 228, Red No. 405, Orange No. 203, Yellow No. 205, Yellow No. 4, Yellow No. 5, Blue No. 1, Blue No. 404 and Green No. 3; natural colorants such as chlorophyll and β-carotene; and dyes. Use can also be made of any of these that has been hydrophobized with silicone or the like.

In addition, examples of other organic particles include crosslinked silicone powders (i.e., so-called silicone rubber powders consisting of an organopolysiloxane having a structure in which repeating chains of diorganosiloxane units are crosslinked), and silicone resin particles (polyorganosilsesquioxane resin particles having a three-dimensional network structure). Specific examples are known by such names as (dimethicone:vinyl dimethicone) crosspolymer and polymethylsilsesquioxane. These are commercially available as powders or as silicone oil-containing swollen materials. Examples include the products sold under the trade names KMP-598, 590, 591 and KSG-016F (all from Shin-Etsu Chemical Co., Ltd.). One, two or more of these powders may be used.

In particular, silicone resin-coated silicone rubber powders are used in sunscreens, makeup, concealers and the like on account of their tactile feel-enhancing effects such as preventing a sticky feel on the skin and their shape-correcting effects on wrinkles, pores and the like. Specific examples of silicone resin-coated silicone rubber powders include those known by such names as (vinyl dimethicone/methicone silsesquioxane) crosspolymer, (diphenyl dimethicone/vinyldiphenyl dimethicone/silsesquioxane) crosspolymer, polysilicone-22 and polysilicone-1 crosspolymer, as defined in the Cosmetic-Info.jp (https://www.cosmetic-info.jp) database. These are commercially available under such trade names as KSP-100, 101, 102, 105, 200, 411 and 441 (all from Shin-Etsu Chemical Co., Ltd.). One, two or more of these powders may be used.

<Finely Divided Metal Oxide>

The finely divided metal oxide used in this invention is not particularly limited, provided that it is a starting material which can generally be included in cosmetics. Examples include one, two or more metal oxides selected from among titanium dioxide, zinc oxide and cerium oxide. This metal oxide may be a composite powder of two or more from among titanium dioxide, zinc oxide and cerium oxide, or a composite powder with another powder. The average primary particle size is preferably not more than 200 nm, and more preferably not more than 120 nm. At a particle size larger than this, the UV protection function decreases and a white residue forms. The average primary particle size can be measured using, for example, transmission electron micrographs.

The finely divided metal oxide may be untreated or may have a known surface treatment that is used in ordinary cosmetics, and is not particularly limited in this respect. Examples of inorganic treatment include silica coating and alumina coating. Examples of organic treatment include silanes or silylating agents such as caprylyl silane (AES-3083, from Shin-Etsu Chemical Co., Ltd.); silicone oils such as dimethyl silicone (the KF-96AK series from Shin-Etsu Chemical Co., Ltd.), methyl hydrogen polysiloxanes (e.g., KF-99P and KF-9901, from Shin-Etsu Chemical Co., Ltd.), and silicone-branched silicone treatment agents (e.g., KF-9908, KF-9909, from Shin-Etsu Chemical Co., Ltd.); waxes, paraffins, organofluorine compounds such as perfluoroalkyls, surfactants, amino acids such as N-acylglutamic acid, and metallic soaps such as aluminum stearate and magnesium myristate. In particular, KF-9909 (Shin-Etsu Chemical Co., Ltd.) exhibits a high dispersity both in silicones and in oils, and thus is used in sunscreens and foundations. These surface treatments may be used singly or two or more may be used in combination according to the intended purpose.

Commercial products may also be used as these surface-treated finely divided metal oxides. For example, finely divided titanium dioxide is commercially sold under the trade names MT-01, 05, 100Z, 100TV, 100AQ, 150EX, 500B, 505SAS, 700B, 014Z and SMT-500SAS (Tayca Corporation); ST-455, 455WS, 457ECS and 495M (Titan Kogyo, Ltd.); and TTO-S1, S4, 51(C), 55(A), 55(C) and 80(A) (Ishihara Sangyo Kaisha, Ltd.). Finely divided zinc oxide is commercially sold under the trade names MZ-150, 200, 300, 306X, 500HP, 505T, 506X, MZY-203S, 210M3S, TMZ-HA1 and MZX-5080TS (Tayca Corporation); and FZO-50 (Ishihara Sangyo Kaisha, Ltd.).

The amount of finely divided metal oxide included in the invention is not particularly limited, although including from 0.1 to 50 wt %, based on the overall weight of the cosmetic composition, is preferred; in terms of usability, including from 1 to 35 wt % is more preferred. At less than 0.1 wt %, a sufficient UV-blocking effect cannot be obtained. When more than 50 wt % is included, the spreadability during use may worsen, or the cosmetic film may take on a white or dry powdery aspect.

<Other Optional Ingredients>

Various ingredients ordinarily used in cosmetic compositions may be included in the cosmetic composition of the invention within a range that does not detract from the advantageous effects of the invention. Among the ingredients that may be included are (1) oils, (2) compounds having alcoholic hydroxyl groups, (3) film-forming agents, (4) surfactants, (5) compositions that include a crosslinked organopolysiloxane and an oil that is liquid at room temperature, (6) silicone waxes, and (7) other additives. These ingredients may be of one type used alone or of two or more types used in a suitable composition. These ingredients are suitably selected and used according to such considerations as the type of cosmetic; the amount in which an ingredient is included (content) may be set to, for example, a known content for the type of cosmetic.

(1) Oils

The oils may be solid, semisolid or liquid. For example, natural plant and animal oils and fats and semi-synthetic oils and fats, hydrocarbon oils, higher alcohols, ester oils, silicone oils and fluorinated oils may be used.

Natural Plant and Animal Oils and Fats:

Examples of natural plant and animal oils and fats and semi-synthetic oils and fats include avocado oil, linseed oil, almond oil, Chinese wax, perilla oil, olive oil, cocoa butter, kapok wax, kaya oil, carnauba wax, liver oil, candelilla wax, refined candelilla wax, beef tallow, neatsfoot oil, beef bone fat, hydrogenated beef tallow, apricot kernel oil, spermaceti, hydrogenated oil, wheat germ oil, sesame oil, rice germ oil, rice bran oil, sugarcane wax, camellia kissi oil, safflower oil, shea butter, Chinese tung oil, cinnamon oil, jojoba wax, squalane, squalene, shellac wax, turtle oil, soybean oil, teaseed oil, camellia Japonica seed oil, evening primrose oil, corn oil, lard, rapeseed oil, Japanese tung oil, rice bran wax, germ oil, chicken fat, persic oil, palm oil, palm kernel oil, castor oil, hydrogenated castor oil, castor oil fatty acid methyl esters, sunflower oil, grapeseed oil, bayberry tallow, jojoba oil, macadamia nut oil, beeswax, mink oil, meadowfoam seed oil, cottonseed oil, cotton wax, Japan wax, sumac kernel oil, montan wax, coconut oil, hydrogenated coconut oil, coconut oil fatty acid triglycerides, mutton tallow, peanut oil, lanolin, liquid lanolin, reduced lanolin, lanolin alcohol, hydrogenated lanolin, acetylated lanolin, acetylated lanolin alcohol, isopropyl lanolates, polyoxyethylene lanolin alcohol ether, polyoxyethylene lanolin alcohol acetate, polyethylene glycol lanolate, polyoxyethylene hydrogenated lanolin alcohol ether and egg yolk oil.

Hydrocarbon Oils:

Hydrocarbon oils are exemplified by linear or branched hydrocarbon oils, and may be volatile hydrocarbon oils or nonvolatile hydrocarbon oils. Illustrative examples include ozokerite, α-olefin oligomers, light isoparaffins, isododecane, isohexadecane, light liquid isoparaffins, squalane, synthetic squalane, vegetable squalane, squalene, ceresin, paraffin, paraffin wax, polyethylene wax, polyethylene-polypropylene wax, ethylene-propylene-styrene copolymers, butylene-propylene-styrene copolymers, liquid paraffin, liquid isoparaffin, pristane, polyisobutylene, hydrogenated polyisobutene, microcrystalline wax and petrolatum; and higher fatty acids such as lauric acid, myristic acid, palmitic acid, stearic acid, behenic acid undecylenic acid, oleic acid, linoleic acid, linolenic acid, arachidonic acid, eicosapentaenoic acid (EPA), docosahexaenoic acid (DHA), isostearic acid and 12-hydroxystearic acid.

Higher Alcohols:

Higher alcohols include alcohols having preferably at least 6 carbon atoms, and more preferably from 10 to 30 carbon atoms. Illustrative examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, polyoxyethylene cholesterol ether, glycerol monostearyl ether (batyl alcohol) and glyceryl monooleyl ether (selachyl alcohol).

Ester Oils:

Examples of ester oils include diisobutyl adipate, 2-hexyldecyl adipate, 2-heptylundecyl adipate, N-alkyl glycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dioctanoate, neopentyl glycol dicaprylate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, fatty acid esters of dipentaerythritol, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, isopropyl lauroyl sarcosinate and diisostearyl malate; and glyceride oils such as acetoglyceryl, glyceryl triisocotanoate, glyceryl triisostearate, glyceryl triisopalmitate, glyceryl tribehenate, glyceryl monostearate, glyceryl di-2-heptylundecanoate, glyceryl trimyristate and diglyceryl myristate isostearate.

Silicone Oils:

Silicone oils are not particularly limited, provided they are starting materials that can normally be included in cosmetics. Examples include low-viscosity to high-viscosity linear or branched organopolysiloxanes such as dimethylpolysiloxane, cyclopentasiloxane, cyclohexasiloxane, disiloxane, trisiloxane, methyl trimethicone, caprylyl methicone, methylphenyl polysiloxane, methylhexyl polysiloxane, methyl hydrogen polysiloxane and dimethylsiloxane-methylphenylsiloxane copolymers; silicone rubbers such as amino-modified organopolysiloxane, pyrrolidone-modified organopolysiloxane, pyrrolidone carboxylic acid-modified organopolysiloxane, high degree of polymerization gum-like dimethylpolysiloxane, gum-like amino-modified organopolysiloxane and gum-like dimethylsiloxane-methylphenylsiloxane copolymers, as well as cyclic organopolysiloxane solutions of silicone gums and rubbers, trimethylsiloxysilicic acid and cyclic siloxane solutions of trimethylsiloxysilicic acid, higher alkoxy-modified silicones such as stearoxysilicone, higher fatty acid-modified silicones, alkyl-modified silicones, long chain alkyl-modified silicones, amino acid-modified silicones, fluorine-modified silicones, silicone resins, and decomposition products of silicone resins. Of these, preferred use is made of volatile silicones which provide a refreshing feel during use (such as the commercial products TMF-1.5, KF-995 and KF-96A-2cs from Shin-Etsu Chemical Co., Ltd.), and phenyl silicones (such as the commercial products KF-56A and 54HV from Shin-Etsu Chemical Co., Ltd.) which are used to improve compatibility with other oils and to import gloss. One, two or more silicone oils may be used.

Fluorinated Oils:

Examples of fluorinated oils include perfluoropolyethers, perfluorodecalin and perfluorooctane.

(2) Alcoholic Hydrogen Group-Containing Compounds

Examples of alcoholic hydroxyl group-containing compounds include lower alcohols having preferably from 2 to 5 carbon atoms, such as ethanol and isopropanol; and sugar alcohols such as sorbitol and maltose. Additional examples include sterols such as cholesterol, sitosterol, phytosterol and lanosterol; and polyhydric alcohols such as butylene glycol, propylene glycol, dibutylene glycol, pentylene glycol, decanediol, octanediol and hexanediol.

(3) Film-Forming Agents

The film-forming agent is not particularly limited, provided it is a starting material that can normally be included in cosmetics. Specific examples include latexes of, for example, polyvinyl alcohol, polyvinylpyrrolidone, polyvinyl acetate or polyalkyl acrylate; dextrin, cellulose derivatives such as alkyl cellulose and nitrocellulose, siliconized polysaccharides such as pullulan tri(trimethylsiloxy)silylpropylcarbamate, acrylic-silicone graft copolymers such as alkyl acrylate-dimethicone copolymers, silicone resins such as trimethylsiloxysilicic acid, silicone-modified polynorbonene, silicone resins such as fluorine-modified silicone resins, fluorocarbon resins, aromatic hydrocarbon resins, polymer emulsion resins, terpene resins, polybutene, polyisoprene, alkyd resins, polyvinylpyrrolidone-modified polymers, rosin-modified resins and polyurethanes.

Of these, a silicone-based film-forming agent is preferred. Examples of such film-forming resins that can be used include, but are not limited to, pullulan tri(trimethylsiloxy) silylpropylcarbamate (commercially available dissolved in a solvent as, for example, TSPL-30-D5 and ID from Shin-Etsu Chemical Co., Ltd.), alkyl acrylate-dimethicone copolymers (commercially available dissolved in a solvent as, for example, KP-543, 545, 549, 550 and 545L from Shin-Etsu Chemical Co., Ltd.), trimethylsiloxysilicic acid (commercially available dissolved in a solvent as, for example, KF-7312J and X-21-5250 from Shin-Etsu Chemical Co., Ltd.), and silicone-modified to polynorbonene (commercially available dissolved in a solvent as, for example, NBN-30-ID from Shin-Etsu Chemical Co., Ltd.). One, two or more film-forming agents may be used.

(4) Surfactants

Examples of surfactants include, without particular limitation, nonionic, anionic, cationic and amphoteric surfactants. Use can be made of any surfactant that is used in conventional cosmetics. Of these surfactants, partially crosslinked polyether-modified silicones, partially crosslinked polyglycerin-modified silicones, linear or branched polyoxyethylene-modified organopolysiloxanes, linear or branched polyoxyethylene-polyoxypropylene-modified organopolysiloxanes, linear or branched polyoxyethylene/alkyl-co-modified organopolysiloxanes, linear or branched polyoxyethylene-polyoxypropylene/alkyl-co-modified organopolysiloxanes, linear or branched polyglycerin-modified organopolysiloxanes and linear or branched polyglycerol/alkyl-co-modified organopolysiloxanes are preferred. The content of hydrophilic polyoxyethylene groups, polyoxyethylene-polyoxypropylene groups or polyglycerol residues in these surfactants is preferably from 10 to 70 wt % of the molecule. Examples include the following products available from Shin-Etsu Chemical Co. Ltd.: KSG-210, 240, 310, 320, 330, 340, 320Z, 350Z, 710, 810, 820, 830, 840, 820Z, 850Z, KF-6011, 6013, 6043, 6028, 6038, 6048, 6100, 6104 and 6105.

(5) Compositions of a Crosslinked Organopolysiloxane and an Oil that is Liquid at Room Temperature In compositions of a crosslinked organopolysiloxane and an oil that is liquid at room temperature, the crosslinked organopolysiloxane is preferably one that swells by including therein at least its own weight of the liquid oil. Any of the liquid silicone oils, hydrocarbon oils, ester oils, natural plant and animal oils, semi-synthetic oils and fluorinated oils in Ingredient (1) may be used as this liquid oil. Examples include 0.65 to 100 $mm^2/s$ (25° C.) low-viscosity silicone oils, hydrocarbon oils such as liquid paraffin, squalane, isododecane and isohexadecane, glyceride oils such as triethylhexanoin, ester oils such as isotridecyl isononanoate, N-acylglutamates and lauroyl sarcosinates, and natural plant and animal oils such as macadamia nut oil. Ingredient (5) differs from above Ingredient (4) in that it is a compound without a polyether or polyglycerol structure in the molecular structure. Specific examples include KSG-15, 1510, 16, 1610, 18A, 19, 41A, 42A, 43, 44, 042Z, 045Z and 048Z from Shin-Etsu Chemical Co., Ltd.

(6) Silicone Waxes

The silicone wax is preferably an acrylic silicone resin that is an acrylic-silicone graft or block copolymer. Use can be made of acrylic silicone resins containing at least one type of molecule selected from among pyrrolidone moieties, long-chain alkyl moieties, polyoxyalkylene moieties, fluoroalkyl moieties, and the anionic moieties of carboxylic acids. Specific examples include the acrylic-silicone graft copolymers KP-561P and 562-P available from Shin-Etsu Chemical Co., Ltd. These silicone waxes have a smooth spreadability so that they seem to melt on the skin, and also impart the sensation of a film having adherence, a moist feel, and a lustrous feel.

(7) Other Additives

Examples of other additives include oil-soluble gelling agents, antiperspirants, ultraviolet absorbers, moisturizers, antibacterial agents and preservatives, fragrances, salts, antioxidants, pH adjustors, chelating agents, algefacients, anti-inflammatory agents, skin beautifying ingredients (whitening agents, cell activating agents, rough skin improving agents, blood circulation promoters, astringents, antiseborrheic agents, etc.), vitamins, amino acids, water-soluble polymeric compounds, and inclusion compounds.

Oil-Soluble Gelling Agents:

Examples of oil-soluble gelling agents include metallic soaps such as aluminum stearate, magnesium stearate and zinc myristate; amino acid derivatives such as N-lauroyl-L-glutamic acid and α,γ-di-n-butylamine; fatty acid esters of dextrin, such as dextrin palmitate, dextrin stearate and dextrin 2-ethylhexanoate palmitate; fatty acid esters of sucrose, such as sucrose palmitate and sucrose stearate; fatty acid esters of fructooligosaccharides such as fructooligosaccharide stearate and fructooligosaccharide 2-ethylhexanoate; benzilidene derivatives of sorbitol, such as monobenzilidene sorbitol and dibenzilidene sorbitol; and organically modified clay minerals such as dimethylbenzyl dodecylammonium montmorillonite clay and dimethyl dioctadecylammonium montmorillonite clay.

Antiperspirants:

Examples of antiperspirants include aluminum chlorohydrate, aluminum chloride, aluminum sesquichlorohydrate, zirconium hydroxychloride, aluminum zirconium hydroxychloride and aluminum zirconium glycine complex.

Ultraviolet Absorbers:

Examples of ultraviolet absorbers include homomenthyl salicylate, octocrylene, 4-tert-butyl-4'-methoxydibenzoyl methane, 4-(2-β-glucopyranosiloxy)propoxy-2-hydroxybenzophenone, octyl salicylate, 2-[4-(diethylamino)-2-hydroxybenzoyl] hexyl benzoate, dihydroxydimethoxybenzophenone, sodium dihydroxydimethoxybenzophenone disulfonate, dihydroxybenzophenone, dimethicodiethylbenzal malonate, 1-(3,4-dimethoxyphenyl)-4,4-dimethyl-1,3-pentanedione, 2-ethylhexyl dimethoxybenzylidene dioxoimidazolidine propionate, tetrahydroxy benzophenone, terephthalylidene dicamphor sulfonic acid, 2,4,6-tris[4-(2-ethylhexyloxycarbonyl)anilino]-1,3,5-triazine, methylbis(trimethylsiloxy)silylisopentyl trimethoxycinnamate, drometrizole trisiloxane, 2-ethylhexyl p-dimethylaminobenzoate, isopropyl p-methoxycinnamate, 2-ethylhexyl p-methoxycinnamate, 2,4-bis-[{4-(2-ethylhexyloxy)-2-hydroxy}-phenyl]-6-(4-methoxyphenyl)-1,3,5-triazine, 2-hydroxy-4-methoxybenzophenone, hydroxymethoxybenzophenonesulfonic acid and the trihydrate thereof, sodium hydroxymethoxybenzophenonesulfonate, phenylbenzimidazolesulfonic acid and 2,2'-methylenebis[6-(2H-benzotriazol-2-yl)-4-(1,1,3,3-tetramethylbutyl)phenol]. Moreover, a UVA absorber (e.g., diethylamino hydroxybenzoyl hexyl benzoate) and a UVB absorber (e.g., ethylhexyl methoxycinnamate) may be used together.

Moisturizers:

Examples of moisturizers include glycerol, sorbitol, glucose, erythritol, xylitol, maltitol, polyethylene glycol, glyceryl glucoside, hyaluronic acid, chondroitin sulfate, pyrrolidone carboxylate, polyoxyethylene methyl glucoside, polyoxypropylene methyl glycoside, egg yolk lecithin, soybean lecithin, phosphatidylcholine, phosphatidylethanolamine, phosphatidylserine, phosphatidylglycerol, phosphatidylinositol and sphingophospholipid.

Antibacterial Agents and Preservatives:

Examples of antibacterial agents and preservatives include alkyl p-oxybenzoates, benzoic acid, sodium benzoate, sorbic acid, potassium sorbate, phenoxyethanol, imidazolidinyl urea, benzoic acid, salicyclic acid, carbolic acid, alkyl p-oxybenzoates, p-chloro-m-cresol, hexachlorophene, benzalkonium chloride, chlorohexidine chloride, trichlorocarbanilide, iodopropynyl butylcarbamate, polylysine, photosensitizers, silver and plant extracts.

Salts:

Exemplary salts include inorganic salts, organic salts, amine salts and amino acid salts. Examples of inorganic salts include sodium salts, potassium salts, magnesium salts, calcium salts, aluminum salts, zirconium salts and zinc salts of inorganic acids such as hydrochloric acid, sulfuric acid, carbonic acid and nitric acid. Examples of organic salts include salts of organic acids such as acetic acid, dehydroacetic acid, citric acid, malic acid, succinic acid, ascorbic acid and stearic acid. Examples of amine salts and amino acid salts include salts of amines such as triethanolamine and salts of amino acids such as glutamic acid. In addition, use can also be made of the salts of hyaluronic acid and chondroitin sulfate, aluminum zirconium glycine complexes, and neutral salts of acids and alkalis used in cosmetic formulations.

Antioxidant:

Examples of antioxidants include tocopherol, p-t-butylphenol, butylhydroxyanisole, dibutylhydroxytoluene and phytic acid.

pH Adjustors:

Examples of pH adjustors include lactic acid, citric acid, sodium citrate, sodium hydroxide, potassium hydroxide, arginine, glycolic acid, succinic acid, tartaric acid, dl-malic acid, potassium carbonate, sodium bicarbonate and ammonium bicarbonate.

Chelating Agents:

Examples of chelating agents include alanine, sodium edetate, sodium polyphosphate, sodium metaphosphate and phosphoric acid.

Algefacients:

Examples of algefacients include L-menthol and camphor.

Anti-Inflammatory Agents

Examples of anti-inflammatory agents include allantoin, glycyrrhizic acid and salts thereof, glycyrrhetic acid and stearyl glycyrrhetinate, tranexamic acid and azulene.

Skin Beautifying Ingredients:

Examples of skin beautifying ingredients include whitening agents such as placenta extract, albumin, glutathion and saxifraga sarmentosa extract; cell activating agents such as royal jelly, photosensitizers, cholesterol derivatives and calf blood extract; rough skin improving agents, blood circulation promoters such as nonylic acid vanillylamide, benzyl nicotinate, β-butoxyethyl nicotinate, capsaicin, zingerone, Cantherides tincture, ichthammol, caffeine, tannic acid, α-borneol, tocopherol nicotinate, inositol hexanicotinate, cyclandelate, cinnarizine, tolazoline, acetylcholine, verapamil, cepharanthine and γ-oryzanol; astringents such as zinc oxide and tannic acid; and antiseborrheic agents such as sulfur and thianthrol.

Vitamins:

Examples of vitamins include A vitamins such as vitamin A oil, retinol, retinol acetate and retinol palmitate; B vitamins, including the B2 vitamins riboflavin, riboflavin butyrate and flavin adenine dinucleotide, the B6 vitamins pyridoxine hydrochloride, pyridoxine dioctanoate and pyridoxine tripalmitate, vitamin B12 and derivatives thereof, and vitamin B15 and derivatives thereof; C vitamins such as L-ascorbic acid, L-ascorbyl dipalmitate, the sodium salt of L-ascorbic acid 2-sulfate and dipotassium L-ascorbyl phosphate; D vitamins such as ergocalciferol and cholecalciferol; E vitamins such as α-tocopherol, β-tocopherol, γ-tocopherol, dl-α-tocopherol acetate, dl-α-tocopherol nicotinate and dl-α-tocopherol succinate; nicotinic acid compounds such as nicotinic acid, benzyl nicotinate and nicotinamide; vitamin H, vitamin P, pantothenic acid compounds such as calcium pantothenate, D-pantothenyl alcohol, pantothenyl ethyl ether and acetylpantothenyl ethyl ether, and biotin.

Amino Acids:

Examples of amino acids include glycine, valine, leucine, isoleucine, serine, threonine, phenylalanine, arginine, lysine, aspartic acid, glutamic acid, cystine, cysteine, methionine and tryptophan.

Water-Soluble Polymeric Compounds:

Examples of water-soluble polymeric compounds include plant-based macromolecular compounds such as gum arabic, guar gum, carrageenan, agar, quince seed gum, starch, algae colloids, tragacanth gum and locust bean gum; microbial polymeric compounds such as xanthan gum, dextran, succinoglucan and pullulan; animal-based polymeric compounds such as collagen, casein, albumin and gelatin; cellulose-based polymeric compounds such as methylhydroxypropylcellulose, hydroxymethylcellulose, hydroxypropylcellulose and carboxymethylcellulose sodium; alginic acid-based polymeric compounds such as sodium alginate and propylene glycol alginate; vinyl-based polymeric compounds such as (acrylates/$C_{10-30}$ alkyl acrylate) crosspolymers and carboxyvinyl polymers; polyethylene glycol and polyoxyethylene-polyoxypropylene copolymer-type polymeric compounds; acrylic polymeric compounds such as sodium polyacrylate, polyacrylamide, (ammonium acryloyldimethyltaurate/VP) copolymer, (ammonium acryloyldimethyltaurate/beheneth-25 methacrylate) crosspolymer, (sodium acrylate/sodium acryloyldimethyltaurate) copolymer and (hydroxyethyl acrylate/sodium acryloyldimethyltaurate) copolymer, synthetic water-soluble polymeric compounds such as polyethyleneimine and cationic polymers; and inorganic water-swellable minerals such as bentonite, aluminum magnesium silicate, montmorillonite, saponite and hectorite. These water-soluble polymeric compounds may also include substances that are used as film-forming agents, such as polyvinyl alcohol or polyvinyl pyrrolidone. Vinyl-based polymeric compounds and acrylic polymeric compounds are convenient for easily obtaining emulsion stabilizing and thickening effects in aqueous systems and oil-in-water emulsions.

Inclusion Compounds:

An example of an inclusion compound is cyclodextrin.

Of the above-described cosmetics, use in the form of an emulsion composition according to the invention is especially effective. In this case, the emulsion may be in the form of an oil-in-water emulsion, a water-in-oil emulsion, a water-in-oil-in-water emulsion or an oil-in-water-in-oil emulsion.

Alternatively, the cosmetic of the invention may also be used in the form of a nonaqueous composition. The form of the nonaqueous composition is exemplified by solid, semisolid, pressed, mousse, powder and stick forms. In this invention, "nonaqueous composition" refers to compositions that are not formulated with water.

EXAMPLES

Examples and Comparative Examples are given below to more fully illustrate the invention, although the invention is not limited by these Examples. Unless noted otherwise, ingredient amounts are indicated in percent by weight.

Example 1, Comparative Example 1

Creams were prepared according to the formulations shown in Table 1, and the stickiness and moisturizing properties of each were evaluated. The results are presented in Table 1. The evaluation criteria were as follows.

(1) Feel on Use (Stickiness)

An expert panel (10 judges) carried out sensory evaluations of stickiness when a sample (cream) was applied to the cheeks. The rating criteria were set to 5 points when the sample substantially does not feel sticky, 3 points when it feels a little sticky, and 1 point when it clearly feels sticky, and the total score was determined.

O: Total score was 40 points or more
Δ: Total score was from 21 to 39 points
X: Total score was 20 points or less (2) Weight-Average Molecular Weight The polystyrene-equivalent weight-average molecular weights (Mw) of silicone-branched polyglycerin-modified silicones were measured by GPC analysis under the following conditions: Tosoh Corporation columns, TSKgel Super H2500 (1 column) and TSKgel Super HM-N (1 column); solvent, tetrahydrofuran; flow rate, 0.6 mL/min; detector, RI (40° C.); column temperature, 40° C.; injected amount, 50 μL; sample concentration, 0.3 wt %.

TABLE 1

| Ingredients (wt %) | Example 1 | Comparative Example 1 |
|---|---|---|
| Silicone-branched polyglycerin-modified silicone A [1] | 3.0 | — |
| Silicone-branched polyglycerin-modified silicone B [2] | — | 3.0 |
| Dimethylpolysiloxane (6 cs) | 20.0 | 20.0 |

TABLE 1-continued

| Ingredients (wt %) | Example 1 | Comparative Example 1 |
|---|---|---|
| 1,3-Butylene glycol | 7.0 | 7.0 |
| Sodium chloride | 0.5 | 0.5 |
| Purified water | balance | balance |
| Total | 100.0 | 100.0 |
| Feel on use (stickiness) | O | X |
| Weight-average molecular weight | 8,500 | 18,000 |

1) Polyglyceryl-3 polydimethylsiloxyethyl dimethicone: Mw=8.500 (invention)
2) Polyglyceryl-3 polydimethylsiloxyethyl dimethicone: Mw=18.000 (conventional product)

The results in Table 1 demonstrate that the silicone-branched polyglycerin-modified silicone of the invention was clearly less sticky than the conventional product.

Example 2, Comparative Example 21

Pastes were prepared according to the formulations shown in Table 2, and their viscosities were compared. In the sample dispersing step, the composition was passed twice through a three-roll mill, thereby giving a paste.

(3) Viscosity

The viscosity was measured with a Brookfield viscometer. Measurement was carried out after 6 rotations over 60 seconds using a T-F spindle. The viscosity units are mPa·s.

TABLE 2

| Ingredients (wt %) | Example 2 | Comparative Example 2 |
|---|---|---|
| Silicone-branched polyglycerin-modified silicone A [1] | 1.0 | — |
| Silicone-branched polyglycerin-modified silicone B [2] | — | 1.0 |
| Metallic soap-treated finely divided titanium dioxide* | 19.0 | 19.0 |
| Dimethylpolysiloxane (6 cs) | balance | balance |
| Total | 30.0 | 30.0 |
| Viscosity one week after preparation | 20,000 | 45,000 |
| Weight-average molecular weight | 8,500 | 18,000 |

*MT-100Z (Tayca Corporation)

The results in Table 2 demonstrate that the paste has a low viscosity and the silicone-branched polyglycerin-modified silicone of the invention has an excellent dispersibility, enabling a lower viscosity paste to be prepared. The degree of freedom in formulation increases owing in part to an improvement in the dispersibility of the paste.

Example 3, Comparative Example 31

Slurries were prepared according to the formulations shown in Table 3 using a paint shaker (diameter of mixing medium, 1.5 mm).

(4) Viscosity

The viscosity was measured with a Brookfield viscometer. Measurement was carried out after 30 rotations over 60 seconds using an LV-3 spindle. The viscosity units are mPa·s.

TABLE 3

| Ingredients (wt %) | Example 3 | Comparative Example 3 |
|---|---|---|
| Silicone-branched polyglycerin-modified silicone A [1) | 10.0 | — |
| Silicone-branched polyglycerin-modified silicone B [2) | — | 10.0 |
| Metallic soap-treated finely divided titanium dioxide* | 40.0 | 40.0 |
| Decamethylcyclopentasiloxane | balance | balance |
| Total | 100.0 | 100.0 |
| Viscosity immediately after preparation | 78 | 273 |
| Viscosity one month after preparation | 86 | 296 |
| Weight-average molecular weight | 8,500 | 18,000 |

*ST-455 (Titan Kogyo, Ltd)

The results in Table 3 demonstrate that the silicone-branched polyglycerin-modified silicone of the invention has an outstanding dispersibility, enabling a stable slurry to be prepared at a lower viscosity. These results demonstrate that by including the silicone-branched polyglycerin-modified silicone of the invention, the stickiness distinctive to surfactants is reduced and, in formulations containing a powder, especially a finely divided metal oxide, the powder can be stably dispersed even at a lower viscosity, enabling the stability and usability of the cosmetic to be improved.

Example 4

Oil-in-Water Sunscreen Cream
<Preparation of Cosmetic>
  A: Ingredients (1) to (3) were uniformly mixed with a paint shaker.
  B: Component A and Ingredients (4) to (6) were uniformly mixed.
  C: Ingredients (7) to (17) were uniformly mixed
  D: Component B was added to Component C and emulsification carried out, following which Ingredient (18) was added and uniform mixing was carried out, thereby giving an oil-in-water sunscreen.

| | | |
|---|---|---|
| (1) | Silicone-branched polyglycerin-modified silicone [3) | 0.5% |
| (2) | Silicone-treated finely divided zinc oxide | 5 |
| (3) | Decamethylcyclopentasiloxane | 5 |
| (4) | Ethylhexyl methoxycinnamate | 5 |
| (5) | Methylphenylpolysiloxane [4) | 3 |
| (6) | Cetanol | 0.5 |
| (7) | Polyoxyethylene sorbitan monooleate | 2.5 |
| (8) | Glyceryl stearate (SE) | 0.5 |
| (9) | PEG-11 methyl ether dimethicone [5) | 1 |
| (10) | Dipropylene glycol | 6 |
| (11) | 1,3-Butylene glycol | 6 |
| (12) | Carboxyvinyl polymer | 0.3 |
| (13) | Acrylic polymeric compound | 0.3 |
| (14) | Methylparaben | 0.2 |
| (15) | Phenoxyethanol | 0.3 |
| (16) | Disodium edetate | suitable amount |
| (17) | Purified water | balance |
| (18) | 10% Aqueous solution of sodium hydroxide | suitable amount |
| | Total | 100.0 |

3) KF-6106 (Shin-Etsu Chemical Co., Ltd.)
4) KF-56A (Shin-Etsu Chemical Co., Ltd.)
5) KF-6011P (Shin-Etsu Chemical Co., Ltd.)

This sunscreen had a high transparency, little stickiness, and a good feel on use.

Example 5

Water-in-Oil Cream
  A: Ingredients (1) to (4) were uniformly mixed.
  B: Ingredients (5) to (10) were uniformly mixed
  C: Component B was added to Component A and emulsification carried out, giving a water-in-oil emulsion.

| | | |
|---|---|---|
| (1) | Crosslinked polyglycerol-modified silicone [6) | 4% |
| (2) | Crosslinked dimethylpolysiloxane [7) | 1 |
| (3) | Silicone-branched polyglycerin-modified silicone [3) | 3 |
| (4) | Dimethylpolysiloxane (6 cs) | 13 |
| (5) | 1,3-Butylene glycol | 8 |
| (6) | Ethanol | 5 |
| (7) | Phenoxyethanol | 0.3 |
| (8) | Sodium citrate | suitable amount |
| (9) | Sodium chloride | suitable amount |
| (10) | Purified water | balance |
| | Total | 100.0 |

6) KSG-710 (Shin-Etsu Chemical Co., Ltd)
7) KSG-15 (Shin-Etsu Chemical Co., Ltd)

This cream had a moisturizing feel and also had a good feel on use. When the silicone-branched polyglycerin-modified silicone of the invention is substituted with a conventional substance, the cream that uses the conventional substance, as with the results shown in Table 1, becomes a cream that clearly feels sticky.

Example 6

Water-in-Oil Shaking Sunscreen
<Preparation of Cosmetic>
  A: Ingredients (1), (3) and (5) were uniformly mixed with a paint shaker.
  B: Ingredients (2), (4) and (6) were uniformly mixed with a paint mixer.
  C: Components A and B and Ingredients (7) to (12) were uniformly mixed.
  D: Components (13) to (18) were uniformly mixed.
  E: Component D was added to Component C and emulsification was carried out, giving a water-in-oil sunscreen.

| | | |
|---|---|---|
| (1) | Silicone-branched polyglycerin-modified silicone [3) | 2.8% |
| (2) | Silicone-branched polyglycerin-modified silicone [3) | 1.7 |
| (3) | Metallic soap-treated finely divided titanium dioxide | 14 |
| (4) | Hydrogen dimethicone-treated finely divided zinc oxide | 21 |
| (5) | Decamethyl cyclopentasiloxane | 12 |
| (6) | Decamethylcyclopentasiloxane | 12 |
| (7) | Crosslinked dimethylpolysiloxane [7) | 2 |
| (8) | Crosslinked dimethylpolysiloxane [8) | 4 |
| (9) | Silicone-branched polyglycerin-modified silicone [3) | 0.5 |
| (10) | Decamethylcyclopentasiloxane | balance |
| (11) | Dimethylpolysiloxane (6 cs) | 3 |
| (12) | Isotridecyl isononanoate | 4.8 |
| (13) | Silicone composite powder [9) | 1 |
| (14) | 1,3-Butylene glycol | 2 |
| (15) | Phenoxyethanol | suitable amount |

-continued

| | | |
|---|---|---|
| (16) | Sodium citrate | suitable amount |
| (17) | Sodium chloride | suitable amount |
| (18) | Purified water | 13 |
| | Total | 100.0 |

8) KSG-16 (Shin-Etsu Chemical Co., Ltd.)
9) KSG-105 (Shin-Etsu Chemical Co., Ltd.)
Viscosity measurement conditions: Brookfield viscometer, spindle LV-3, after 60 rotations over 60 seconds
Initial viscosity: 209 mPa·s
Viscosity after one month at 50° C.: 246 mPa·s In spite of the high loading of finely divided powder, this sunscreen had a low viscosity, a high transparency and a good, non-sticky feel on use. Moreover, the rise in viscosity at high temperature was suppressed, making for an excellent stability.

Example 7

Water-in-Oil Liquid Foundation
A: Ingredients (7) to (14) were formed into a paste on a three-roll mill.
B: Component A and Ingredients (1) to (6) were uniformly mixed.
C: Ingredients (15) to (19) were uniformly mixed.
D: Component C was added to Component B and emulsification was carried out, giving a water-in oil liquid foundation.

| | | |
|---|---|---|
| (1) | Crosslinked polyether-modified silicone [10] | 3% |
| (2) | Crosslinked dimethylpolysilicone [7] | 7 |
| (3) | Silicone-branched polyether-modified silicone [11] | 2 |
| (4) | Alkyl/silicone-branched polyether-modified silicone [12] | 1 |
| (5) | Decamethylcyclopentasiloxane | balance |
| (6) | Organically modified clay mineral | 1 |
| (7) | Silicone-branched polyglycerin-modified silicone [3] | 1 |
| (8) | Dimethyl polysiloxane (6 cs) | 5 |
| (9) | Isotridecyl isononanoate | 7 |
| (10) | Silicone-treated titanium dioxide [12] | 8.5 |
| (11) | Silicone-treated yellow iron oxide [13] | 1 |
| (12) | Silicone-treated red iron oxide [13] | 0.4 |
| (13) | Silicone-treated black iron oxide [13] | 0.1 |
| (14) | Metallic soap-treated finely divided titanium dioxide | 5 |
| (15) | Dipropylene glycol | 5 |
| (16) | Phenoxyethanol | 0.2 |
| (17) | Sodium citrate | suitable amount |
| (18) | Magnesium sulfate | suitable amount |
| (19) | Purified water | 33 |
| | Total | 100.0 |

10) KSG-210 (Shin-Etsu Chemical Co., Ltd.)
11) KF-6028P (Shin-Etsu Chemical Co., Ltd.)
12) KF-6038 (Shin-Etsu Chemical Co., Ltd.)
13) KF-9909-treated (Shin-Etsu Chemical Co., Ltd.)
Viscosity measurement conditions: Brookfield viscometer, spindle LV-4, after 6 rotations over 60 seconds
Initial viscosity: 9,100 mPa·s
Viscosity after one month at 50° C.: 9,900 mPa·s In spite of the high loading of powder, this liquid foundation has a low viscosity, the spreadability was good, and the feel at use was good. Moreover, the rise in viscosity at high temperature was suppressed, making for an excellent stability.

Example 8

Water-in-Oil Cream Foundation
A: Ingredients (8) to (15) were formed into a paste on a three-roll mill.
B: Component A and Ingredients (1) to (7) were uniformly mixed with a paint mixer.
C: Ingredients (16) to (20) were uniformly mixed.
D: Component C was added to Component B and emulsification was carried out, giving a water-in-oil cream foundation.

| | | |
|---|---|---|
| (1) | Crosslinked polyether-modified silicone [14] | 3% |
| (2) | Crosslinked dimethylpolysilicone [7] | 7 |
| (3) | Alkyl/silicone-branched polyether-modified silicone [12] | 3 |
| (4) | Decamethylcyclopentasiloxane | balance |
| (5) | Ethylhexyl methoxycinnamate | 4 |
| (6) | Diethylamino hydroxybenzoyl hexyl benzoate | 1 |
| (7) | Organically modified clay mineral | 1.2 |
| (8) | Silicone-branched polyglycerin-modified silicone [3] | 1.5 |
| (9) | Methylphenylpolysiloxane [4] | 10 |
| (10) | Isotridecyl isononanoate | 7 |
| (11) | Silicone-treated titanium dioxide [12] | 8.5 |
| (12) | Silicone-treated yellow iron oxide [13] | 1 |
| (13) | Silicone-treated red iron oxide [13] | 0.4 |
| (14) | Silicone-treated black iron oxide [13] | 0.1 |
| (15) | Metallic soap-treated finely divided titanium dioxide | 10 |
| (16) | Dipropylene glycol | 5 |
| (17) | Phenoxyethanol | 0.2 |
| (18) | Sodium citrate | suitable amount |
| (19) | Magnesium sulfate | suitable amount |
| (20) | Purified water | 30 |
| | Total | 100.0 |

14) KSG-240 (Shin-Etsu Chemical Co., Ltd.)

Although this cream foundation had a high loading of powder, the spreadability was good and the feel on use was also good.

Example 9

Nonaqueous Concealer
A: Ingredients (7) to (12) were formed into a paste on a three-roll mill.
B: Component A and Ingredients (1) to (6) were uniformly mixed, giving a nonaqueous concealer.

| | | |
|---|---|---|
| (1) | Silicone composite powder [15] | 23% |
| (2) | Phenyl-modified silicone composite powder [16] | 5 |
| (3) | Crosslinked dimethylpolysiloxane [17] | 6 |
| (4) | Dimethylpolysiloxane (6 cs) | 40 |
| (5) | Methylphenylpolysiloxane [4] | 7 |
| (6) | Decamethylcyclopentasiloxane | balance |
| (7) | Triethylhexanoin | 0.2 |
| (8) | Silicone-branched polyglycerin-modified silicone [3] | 0.5 |
| (9) | Silicone-modified titanium dioxide [12] | 0.3 |
| (10) | Silicone-modified yellow iron oxide [13] | suitable amount |
| (11) | Silicone-modified red iron oxide [13] | suitable amount |
| (12) | Silicone-modified black iron oxide [13] | suitable amount |
| | Total | 100.0 |

15) KSP-101 (Shin-Etsu Chemical Co., Ltd.)
16) KSP-300 (Shin-Etsu Chemical Co., Ltd.)
17) KSG-19 (Shin-Etsu Chemical Co., Ltd.)

This concealer had a good powder dispersibility and the feel on use was also good.

Example 10

Lipstick
A: Ingredients (1) to (6) were heated to 95° C. and uniformly mixed.
B: Ingredients (7) to (9) were added to Component A and uniformly mixed after heating to 70° C.
C: Ingredients (10) to (17) were dispersed on a three-roll mill, added to Component B, heated to 70° C. and uniformly mixed, following which the mixture was cooled to room temperature, giving a lipstick.

| | | |
|---|---|---|
| (1) | Candelilla wax | 8.6% |
| (2) | Polyethylene | 5 |
| (3) | Microcrystalline wax | 0.8 |
| (4) | Silicone wax [18] | 8.2 |
| (5) | Macadamia nut oil | 6.6 |
| (6) | Isotridecyl isononanoate | 4.5 |
| (7) | Acrylic-silicone graft copolymer [19] | 40 |
| (8) | Silicone-branched polyglycerin-modified silicone [3] | 0.5 |
| (9) | Decamethylcyclopentasiloxane | balance |
| (10) | Diisostearyl malate | 6 |
| (11) | Red No. 201 | 0.3 |
| (12) | Red No. 202 | 0.4 |
| (13) | Yellow No. 4 | 1.2 |
| (14) | Silicone-treated titanium dioxide [12] | 2.9 |
| (15) | Silicone-treated black iron oxide [13] | 0.2 |
| (16) | Silicone-treated red ion oxide [13] | 0.7 |
| (17) | Mica | 7.3 |
| | Total | 100.0 |

18) KP-561P (Shin-Etsu Chemical Co., Ltd.)
19) KP-545 (Shin-Etsu Chemical Co., Ltd.)

This lipstick had excellent adherence and the feel on use was also good. This demonstrates that use in other nonaqueous oil-based cosmetics such as glosses, stick concealers and fluid foundations is also possible.

The invention claimed is:

1. A cosmetic composition comprising polyglyceryl-3 polydimethylsiloxyethyl dimethicone having a polystyrene-equivalent weight-average molecular weight, as determined by gel permeation chromatography, which is not more than 10,000, wherein the cosmetic composition comprises from 0.1 to 20 wt % of polyglyceryl-3 polydimethylsiloxyethyl dimethicone, based on the overall cosmetic composition, and wherein the cosmetic composition is an emulsified composition.

2. The cosmetic composition of claim 1, wherein the polystyrene-equivalent weight-average molecular weight is measured by gel permeation chromatographic analysis under the following conditions: Tosoh Corporation columns, TSKgel Super H2500 and TSKgel Super HM-N; solvent, tetrahydrofuran; flow rate, 0.6 mL/min; detector, RI (40° C.); column temperature, 40° C.; injected amount, 50 μL; sample concentration, 0.3 wt %.

3. The cosmetic composition of claim 1, further comprising one, two or more types of powder.

4. The cosmetic composition of claim 3, wherein the powder is a finely divided metal oxide having an average primary particle size of 200 nm or less.

5. The cosmetic composition of claim 1 which is a nonaqueous composition.

6. The cosmetic composition of claim 1, wherein the polystyrene-equivalent weight-average molecular weight is 5,000 to 8,500.

7. The cosmetic composition of claim 4 which contains from 0.1 to 50 wt % of the finely divided metal oxide, based on the overall cosmetic composition.

* * * * *